(12) United States Patent
Jugl et al.

(10) Patent No.: US 12,138,428 B1
(45) Date of Patent: Nov. 12, 2024

(54) ELECTRONIC ADD-ON MODULE AND ASSEMBLY OF AN ELECTRONIC ADD-ON MODULE AND A DRUG DELIVERY DEVICE

(71) Applicant: Sanofi, Paris (FR)

(72) Inventors: Michael Jugl, Frankfurt am Main (DE); Martin Vitt, Frankfurt am Main (DE); Paul Hayton, Bristol (GB); Ralph Donald Quentin Collings, Bristol (GB); Jakub Sekula, Bristol (GB)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 18/421,659

(22) Filed: Jan. 24, 2024

(51) Int. Cl.
*A61M 5/24* (2006.01)
*A61M 5/31* (2006.01)
*A61M 5/315* (2006.01)

(52) U.S. Cl.
CPC ........ *A61M 5/2422* (2013.01); *A61M 5/3155* (2013.01); *A61M 2005/3126* (2013.01); *A61M 2205/581* (2013.01)

(58) Field of Classification Search
CPC .............. A61M 5/2422; A61M 5/3155; A61M 2005/3126; A61M 2205/581
See application file for complete search history.

(56) References Cited

U.S. PATENT DOCUMENTS

| | | | |
|---|---|---|---|
| 5,693,027 A | 12/1997 | Hansen et al. | |
| 6,663,602 B2 | 12/2003 | Moller | |
| 7,241,278 B2 | 7/2007 | Moller | |
| 9,937,294 B2 | 4/2018 | Quinn et al. | |
| 10,232,123 B1* | 3/2019 | Binier | G16H 20/17 |
| 2008/0306446 A1 | 12/2008 | Markussen | |
| 2009/0054839 A1 | 2/2009 | Moller et al. | |
| 2018/0147362 A1 | 5/2018 | Arenas Latorre et al. | |
| 2019/0001060 A1 | 1/2019 | Gylleby et al. | |

(Continued)

FOREIGN PATENT DOCUMENTS

| | | |
|---|---|---|
| EP | 1570876 B1 | 12/2009 |
| EP | 2814547 B1 | 7/2015 |

(Continued)

OTHER PUBLICATIONS

Hamers-Casterman et al., "Naturally occurring antibodies devoid of light chains," Nature, Jun. 3, 1993, 363(6428):446-448.

(Continued)

*Primary Examiner* — Dung T Ulsh
(74) *Attorney, Agent, or Firm* — Fish & Richardson P.C.

(57) ABSTRACT

The present disclosure is directed to an electronic add-on module configured for attachment to a drug delivery device and to an assembly comprising a drug delivery device and an electronic add-on module. The electronic add-on module may comprise a first portion with a main housing defining a longitudinal axis. The module comprises a gripping mechanism allowing attachment to drug delivery device dose dial user interfaces, e.g., a dial grip, and/or drug delivery device injection user interfaces, e.g., a dose button of varying diameters and shapes. The first portion comprises on an inner side of the main housing at least two elastically deformable arms each having a clamping section which is configured to be elastically deflected radially outwards with respect to the longitudinal axis from a unstressed, nominal position to a strained, deflected position.

19 Claims, 3 Drawing Sheets

(56) References Cited

U.S. PATENT DOCUMENTS

| | | | |
|---|---|---|---|
| 2021/0220562 A1* | 7/2021 | Hansen | A61M 5/20 |
| 2021/0330888 A1 | 10/2021 | Bauer et al. | |
| 2021/0330891 A1* | 10/2021 | Byerly | A61M 5/20 |
| 2023/0263959 A1 | 8/2023 | Gazeley et al. | |

FOREIGN PATENT DOCUMENTS

| | | |
|---|---|---|
| EP | 2890434 B1 | 4/2020 |
| WO | WO 2004/068820 A2 | 8/2004 |
| WO | WO 2004/078239 A1 | 9/2004 |
| WO | WO 2005/018629 A1 | 3/2005 |
| WO | WO 2005/018721 A1 | 3/2005 |
| WO | WO 2006/003388 A2 | 1/2006 |
| WO | WO 2006/030220 A1 | 3/2006 |
| WO | WO 2009/132777 A1 | 11/2009 |
| WO | WO 2014/033195 A1 | 3/2014 |
| WO | WO 2015/018629 A1 | 2/2015 |
| WO | WO 2016/198516 A1 | 12/2016 |
| WO | WO 2019/145415 A1 | 8/2019 |

OTHER PUBLICATIONS

Holt et al., "Domain antibodies: proteins for therapy," TRENDS in Biotechnology, Nov. 1, 2003, 21(11):484-490.

Muyldermans, "Single domain camel antibodies: current status," Reviews in Molecular Biotechnology, Jun. 1, 2001, 74(4):277-302.

Needle-based injection systems for medical use Requirements and test methods, Part 1: Needle injection systems, ISO 11608 1:2014(E), Third Edition, Switzerland, ISO, Dec. 15, 2014, pp. 1-13.

Ward et al., "Binding activities of a repertoire of single immunoglobulin variable domains secreted from *Escherichia coli*," Nature, Oct. 12, 1989, 341(6242):544-546.

* cited by examiner

ELECTRONIC ADD-ON MODULE AND ASSEMBLY OF AN ELECTRONIC ADD-ON MODULE AND A DRUG DELIVERY DEVICE

TECHNICAL FIELD

The present disclosure is generally directed to an electronic add-on module and to an assembly of an electronic system, e.g., an electronic add-on module, which is configured to be, e.g., releasably, attached to a drug delivery device like.

BACKGROUND

Electronic add-on modules may be used attached on to a drug delivery device, e.g., a pen-type injection device. Such drug delivery devices often comprise a housing with a container configured to receive a drug or a cartridge filled with a drug, a dose setting unit comprising a dose dial user interface, e.g., a dial grip, at least rotationally moveable with respect to the housing during dose setting and an injection user interface, e.g., a dose button, at least axially moveable with respect to the housing for causing dose dispensing, and a dose delivery unit comprising a plunger at least axially moveable with respect to the housing during dose dispensing.

Electronic add-on modules for releasable attachment to drug delivery devices are generally known and often used to measure relevant data with respect to dose setting and/or dose dispensing. Due to the different dimensions and working principles of known injection devices, especially regarding dose dial user interfaces and injection user interfaces, such add-on modules are typically tailored to fit to one specific drug delivery device. This requires providing different modules for different devices.

An electronic add-on module is known from WO 2016/198516 A1 which comprises a sleeve-like portion to be positioned over a dosage knob or dial grip of an injection device. A resilient padding is provided on the inner surface of the sleeve-like portion. The padding deforms to accommodate the dosage knob within the cavity of the sleeve-like portion.

Further, a monitoring device for attachment to an injection device is known from WO 2019/145415 A1. This add-on device comprises a coupling element adapted for accommodating the push button and the selector of an insulin pen. In order to adapt to the specific form of any dose selector, the coupling element comprises a gasket with an inner orifice, whose inner surface is similar to the external surface of the selector, such that it can slide along it and embrace it achieving a firm attachment thereto. By employing different designs for the gasket, the device can be used with any available model of drug pen. The gasket is a removable element which can be detached from the coupling element for example, to be interchanged with other gaskets for the adaptation of the device for its coupling to different models of drug pens.

SUMMARY

The present disclosure relates to an improved electronic add-on module suitable to be used with various different drug delivery devices and an improved assembly comprising a drug delivery device and such an electronic add-on module.

In some cases, the electronic add-on module comprises a first portion with a first longitudinal axis and may be attached to a portion of a drug delivery device, e.g., an injection pen. According to one aspect of the present disclosure, a dimension, such as the inner diameter, of the first portion can be, e.g., elastically, adapted to fit to different dimensions and/or contours of different drug delivery devices (e.g., the dose dial user interfaces of the devices). In other words, the first portion can assume various inner diameters. This has the benefit of providing an add-on module which fits onto different drug delivery devices without requiring individual adapter parts. Rather, the module is configured to be put, e.g., pressed, onto injectors of varying diameters (e.g., diameters from around 14 mm to 18 mm), providing secure attachment of the module via a friction fit regardless of the drug delivery device dimensions.

The electronic add-on module may be, e.g., releasably, attached to the drug delivery device by releasably fastening means, such as interacting mechanical coupling elements, or by frictional, elastic and/or form fit engagement. An assembly comprises a drug delivery device and an electronic add-on module configured for releasable attachment to the drug delivery device.

The drug delivery device may comprise at least a housing with a container configured to receive a drug or a cartridge filled with a drug. Further, the drug delivery device may comprise a dose setting unit and a dose delivery unit. Suitable drug delivery devices to be used with a module according to the present disclosure are described e.g., in WO 2004/078239 A1, EP 1 570 876 B1, EP 2 814 547 B1, EP 2 890 434 B1, WO 2005/018721 A1, WO 2009/132777 A1, WO 2014/033195 A1, U.S. Pat. Nos. 5,693,027 A, 6,663,602 B2, 7,241,278 B2 or 9,937,294 B2. In addition to manually driven devices, the module may be used with spring driven devices as described in US 2008/306446 A1 or US 2009/054839 A1. However, the present disclosure is not limited to these examples of drug delivery devices. Rather, other drug delivery devices with a stationary and/or operable portion having, for example, a substantially cylindrical shape may be used with the module. For example, the drug delivery devices may comprise a user interface for selecting and/or dispensing a fixed or variable dose of a drug.

The dose setting unit may comprise a dose dial user interface, e.g., a dose dial grip, which is, at least rotationally, e.g., helically, moveable with respect to the housing during dose setting and an injection user interface at least axially moveable with respect to the housing for causing dose dispensing. The injection user interface may be a separate component part, e.g., a dose button, which may be displaced relative to the dose dial user interface for causing dose dispensing. As an alternative, the dose dial user interface and the injection user interface may be portions of one single component part, such as a combined dose dial and injection knob.

The electronic add-on module may further comprise an optional second portion coupled to the first portion allowing relative axial movement parallel to the first longitudinal axis with respect to the first portion. The first portion may define an auxiliary dose dial user interface and may be configured to be releasably attached to the dose dial user interface of the drug delivery device such that the first portion follows the movement of the dose dial user interface and vice versa when attached to the drug delivery device. The second portion may define an auxiliary injection user interface configured to apply pressure onto the injection user interface of the drug delivery device when attached to the drug delivery device.

In one example of the present disclosure, the first portion comprises a main housing and at least two, e.g., three or more, elastically deformable arms which may be deflected from an unstressed, nominal condition into a strained deflected condition when the module is attached to the drug delivery device. The nominal condition is a condition in which no external forces act on the arms such that the arms are in an unstressed, nominal position. Optionally, the arms may be biased radially inwards by means of an elastically deformable member, e.g., an O-ring. In more detail, the first portion may comprise the elastically deformable arms on an inner side of the main housing. The arms may be part of one or more separate component parts or may be integrally formed with the main housing, e.g., by injection molding. In an example, each arm has a first end constrained to the main housing and a clamping section which is configured to be elastically deflected radially outwards with respect to the longitudinal axis of the module from an unstressed, nominal position to a strained deflected position. The clamping sections circumvent a cavity configured to receive a portion of the drug delivery device. When the arms are in their nominal position, the cavity may have a diameter of 14 mm to 15 mm. With such an exemplary configuration, the arms of the module form a gripper mechanism which may act as an interface and adapter, e.g., via a friction fit by means of the arms, between the add-on module and the various drug delivery devices (e.g., injector pens) within a suitable range, allowing secure attachment of the module regardless of the precise size of the drug delivery device interface, which may have a diameter for example between about 14 mm and about 19 mm.

When the arms are in their deflected position, the cavity may have a diameter of 15 mm to 19 mm. The deflection of the clamping sections may be limited to a maximum deflected position, wherein, when the arms are in their maximum deflected position, the cavity may have a diameter of 19 mm to 21 mm.

According to a further aspect of the present disclosure, the arms may comprise a free end opposite to the first end, wherein the clamping section may be provided between the first end and the free end. The free end may have a shoulder protruding radially inwards with respect to the respective clamping section. More specifically, each of the flexible arms may feature a hard shoulder feature at the, e.g., proximally facing, free end, which provides a hard limit to the axial movement of the main housing and ensures repeatable positioning of the module on a drug delivery device. In an example, the module comprises at least three, e.g., four, pairs of two arms each wherein the arms of each pair of arms is connected at the free end by the shoulder. The arms may be connected regardless of the presence of the shoulder, i.e. the shoulders may be separate independent features. If every pair of flexible arms is connected in pairs at their ends by the shoulder, this provides better stiffness of the interface.

In addition or as an alternative, the inner surface of the arms may feature a stepped profile, which enables easier location and reduces insertion force at the beginning stage of attachment, while gradually increasing it as the movement continues.

Optionally, the arms may be provided with features increasing friction between the arms and an interface of a drug delivery device. For example, rubber elements can be molded over the contact surfaces, i.e., the clamping sections, of the gripper arms, which could result in a stronger mechanical connection and a more robust feeling. As an alternative, this effect may be achieved by using a ribbed or rough surface profile on the hard plastic part.

Further, the arms may be provided on a common gripper ring which is constrained in the main housing. The gripper ring may be a substantially cylindrical component integrally formed with the arms. For example, the arms may protrude from a distal edge of the gripper ring. In an example, the first end of the arms is at the distal edge of the gripper ring, the arms extend distally from the respective first ends and are bent radially inwards and such that the respective clamping sections and free ends substantially extend proximally. In other words, the arms may have a U-shape permitting elastic deflection.

Still further, the gripper ring may comprise at least one leaf spring, e.g., four leaf springs, extending proximally from the gripper ring, e.g., from a proximal region of the gripper ring. The leaf spring(s) may extend proximally and radially inwards and may have a bent shape. The leaf springs may be plastic springs integrated into the gripper ring. As an alternative, the integrated plastic springs could be replaced with a conventional metal spring at the expense of increasing the part count and number of assembly steps.

According to an independent aspect of the present disclosure, the electronic add-on module may further comprise an element elastically biasing the clamping sections of the arms radially inwards. For example, an elastomeric band may be wrapped around the outer circumference of the arms and may be configured to exert a force on the arms deflecting the clamping sections radially inwards with respect to the longitudinal axis from the unstressed, nominal position. If an elastomeric band wraps around the circumference of the gripper arms, e.g., retained by molded-in clip features, the band provides a compressive preload force that bends the arms inwards towards the module's longitudinal axis. When the module is attached to an injector pen dial, this increases the friction force and ensures a more secure fit when used with a user interface of the drug delivery device of a diameter at the low end of the design range. When the user interface of the drug delivery device is removed, the band helps return the arms to their nominal position.

In an example, the main (e.g., outer) housing acts as an enclosure for all mechanical components of the module and contains location features that align the moving parts along the module's longitudinal axis. The main housing may comprise on an inner side snap protrusions configured for rotationally and/or axially constraining component parts of the first portion in the main housing. In addition or as an alternative, the main housing may comprise on an inner side ribs configured for axially guiding a component part of the module. For example, on the interior face of the main housing there may be several vertical ribs which axially locate and stabilize the vertical motion of a second portion of the module, e.g., a shuttling button. The exterior face may also feature a ribbed pattern which is intended to assist with securely gripping the module as well as improving aesthetics.

According to a further independent aspect of the present disclosure, the electronic add-on module may comprise a second portion coupled to the first portion allowing relative axial movement parallel to the first longitudinal axis with respect to the first portion. The second portion may be a button partially received in the main housing of the first portion. In an example, the first portion may define an auxiliary dose dial user interface configured to be attached to a dose dial user interface of the drug delivery device, such that the first portion follows the movement of the dose dial user interface and vice versa when attached to the drug delivery device, and the second portion may define an auxiliary injection user interface configured to apply pressure onto an injection user interface of the drug delivery device.

The second portion may be at least partially encased by and retained in the first portion. For example, the first portion may have a cavity receiving at least partially the second portion. The second portion may be axially movable relative to the first portion in a restricted manner preventing full disassembly of the first and second portions. In other words, they can be moved a limited distance relative to each other for operating the drug delivery device. The leaf spring of the gripper ring may bias the second portion in the proximal direction with respect to the first portion. In other words, the leaf springs, e.g., integral plastic leaf springs, may hold the second portion which may be a shuttling button assembly in place while at rest and return it to its neutral position after actuation.

According to an independent aspect of the present disclosure, the second portion may comprise an electrical power source, e.g., a battery or a rechargeable cell, a printed circuit board assembly (PCBA), e.g., comprising and/or forming a control unit, a sensor arrangement, such as an acoustic sensor arrangement comprising e.g., at least one microphone, configured to detect a relative rotational movement between at least two component parts of the drug delivery device, a communication unit for communicating with another device, e.g., for wireless transfer of data, and/or a switch arrangement, e.g., for turning the electronic module on and off and/or for waking the module or its components from a sleeping mode or a low power consumption mode.

An assembly according to the present disclosure comprises a drug delivery device and an electronic add-on module configured for releasable attachment to the drug delivery device.

Preferably, the drug delivery device comprises: a device housing with a container configured to receive a drug or a cartridge filled with a drug, a dose setting unit comprising a dose dial user interface at least rotationally moveable with respect to the device housing during dose setting and an injection user interface at least axially moveable with respect to the device housing for causing dose dispensing, and a dose delivery unit comprising a plunger at least axially moveable with respect to the device housing during dose dispensing.

Although not required in the context of the present disclosure, the drug delivery device may optionally comprise further components such as a drive sleeve, a number sleeve, a clutch, a cap, a needle, a spring, a lead screw or the like, interacting with the dose button, the dose dial grip, the drive sleeve, the plunger and/or the housing, for example as disclosed in WO 2004/078239 A1. However, the present disclosure is not limited to the drug delivery device of WO 2004/078239 A1. Other suitable drug delivery devices to be used with such a module may comprise a dial grip for selecting a variable dose and a separate dose button for initiating or performing dose dispensing, e.g., as described in EP 1 570 876 B1, EP 2 814 547 B1, EP 2 890 434 B1, WO 2009/132777 A1, U.S. Pat. No. 6,663,602 B2, U.S. Pat. No. 7,241,278 B2 or U.S. Pat. No. 9,937,294 B2. In addition, other suitable drug delivery devices to be used with such a module may comprise a single knob forming a dial grip for selecting a variable dose and a dose button for initiating or performing dose dispensing, e.g., as described in WO 2005/018721 A1 or WO 2014/033195 A1. Still further, the drug delivery device may be a spring driven device as described in US 2008/306446 A1 or US 2009/054839 A1.

If the drug delivery device has a similar working principle as in the example of WO 2004/078239 A1, during dose setting components of the drug delivery device may perform the following movements. A housing may be stationary and may be used as a reference system for the further movements of other components. A plunger may be stationary and may be guided in a housing thread. A drive sleeve may be provided rotationally coupled to the dose dial grip during dose setting and rotationally constrained to the housing during dose dispensing. In other words, the drive sleeve may be guided in the housing to perform a purely axial movement during dose dispensing. The drive sleeve may perform a helical movement, i.e. a combined axial and rotational movement, and may be in threaded engagement with the plunger. A dial grip may perform a helical movement. A dose button may be free to rotate but axially constrained to the drive sleeve. For example, the dose button may be axially retained to the drive sleeve by a clutch. An optional clutch may perform a helical movement and may couple a number sleeve to the drive sleeve. An optional clutch spring may perform an axial movement and may be guided in housing splines and may click over clutch teeth. An optional number sleeve may be permanently fixed on the dial grip and may perform a helical movement and may be guided in a housing thread. An optional last dose nut may perform a helical movement on a drive sleeve track of the drive sleeve and may be rotationally constrained to the housing. Hence, the last dose nut may perform axial movement relative to the housing and a helical movement with respect to the drive sleeve.

During dose dispensing components of the drug delivery device may perform the following movements. The housing may remain stationary as a reference system for the further movements of other components. The plunger may perform a helical movement and may be guided in the housing thread. The drive sleeve may perform a pure axial movement and may be in threaded engagement with the plunger. The dose dial grip may perform a helical movement and may be permanently fixed on the number sleeve. The dose button may perform an axial movement if coupled to the drive sleeve and/or the clutch. The optional clutch may perform pure axial movement and may de-couple the number sleeve from the drive sleeve. The optional clutch spring may perform pure axial movement and may be rotationally constrained to the clutch due to a pressure applied to the dose button. The optional number sleeve may perform a helical movement and may be guided in the housing thread. The optional last dose nut may maintain its axial position on the drive sleeve track and may be rotationally constrained to the housing.

In an assembly according to the present disclosure, when the module is attached to the dose dial user interface of the drug delivery device, the clamping sections of the arms may be elastically biased to abut the dose dial user interface in a form fit and/or friction fit.

According to an independent aspect of the present disclosure, the assembly comprises a drug delivery device having a clicker mechanism generating an acoustic feedback signal during specific use conditions, e.g., at least during dose setting. Such a feedback signal may be detected by the electronic module and the module may determine an amount of dose selected and/or dispensed. For example, the clicker mechanism may generate one clicking sound for every IU dispensed, like e.g., in WO 2004/078239 A1, WO 2014/033195 A1, WO 2005/018721 A1 or EP 1 570 876 B1.

The electronic add-on module may be an electronic dose recording system for determining, storing and/or transmitting data indicative of at least a condition of the drug delivery device or its use. For example, the system may detect if the drug delivery device is switched between a dose setting mode and a dose dispensing mode and vice versa. In addition or as an alternative, the system may detect if a dose is set and/or if a dose is dispensed. Still further, the system may detect the amount of dose selected and/or the amount of dose dispensed. In some cases, the electronic add-on module is configured such that it may be switched from a first state having lower energy consumption into a second state having higher energy consumption. This may be achieved by operation of the electronic add-on module, especially by actuating the microswitch. As an alternative, the module may be provided with a wake up functionality which does not require a separate actuation action. The first state may be a sleeping mode and the second mode may be a detection and/or communication mode. As an alternative, an electronic control unit may issue a command, e.g., a signal, to another unit of the electronic dose recording system such that this unit is switched on or rendered operational.

The electronic add-on module may further comprise a communication unit for communicating with another device, e.g., a wireless communications interface for communicating with another device via a wireless network such as Wi-Fi or Bluetooth, or even an interface for a wired communications link, such as a socket for receiving a Universal Serial Bus (USB), mini-USB or micro-USB connector. In some cases, the electronic add-on module comprises an RF, Wi-Fi and/or Bluetooth unit as the communication unit. The communication unit may be provided as a communication interface between the electronic add-on module and the exterior, such as other electronic devices, e.g., mobile phones, personal computers, laptops and so on. For example, dose data may be transmitted by the communication unit to the external device. The dose data may be used for a dose log or dose history established in the external device.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly (A21), Arg (B31), Arg (B32) human insulin (insulin glargine); Lys (B3), Glu (B29) human insulin (insulin glulisine); Lys (B28), Pro (B29) human insulin (insulin lispro); Asp (B28) human insulin (insulin aspart); human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Examples of insulin derivatives are, for example, B29-N-myristoyl-des (B30) human insulin, Lys (B29) (N-tetradecanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des (B30) human insulin, B29-N-omega-carboxypentadecanoyl-gamma-L-glutamyl-des (B30) human insulin (insulin degludec, Tresiba®); B29-N—(N-lithocholyl-gamma-glutamyl)-des (B30) human insulin; B29-N-(ω-carboxyheptadecanoyl)-des (B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g., a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, small modular immunopharmaceuticals (SMIP), binding-domain immunoglobulin fusion proteins, camelized antibodies, and immunoglobulin single variable domains. Additional examples of antigen-binding antibody fragments are known in the art.

The term "immunoglobulin single variable domain" (ISV), interchangeably used with "single variable domain", defines immunoglobulin molecules wherein the antigen binding site is present on, and formed by, a single immunoglobulin domain. As such, immunoglobulin single variable domains are capable of specifically binding to an epitope of the antigen without pairing with an additional immunoglobulin variable domain. The binding site of an immunoglobulin single variable domain is formed by a single heavy chain variable domain (VH domain or VHH domain) or a single light chain variable domain (VL domain). Hence, the antigen binding site of an immunoglobulin single variable domain is formed by no more than three CDRs.

An immunoglobulin single variable domain (ISV) can be a heavy chain ISV, such as a VH (derived from a conventional four-chain antibody), or VHH (derived from a heavy-chain antibody), including a camelized VH or humanized VHH. For example, the immunoglobulin single variable domain may be a (single) domain antibody, a "dAb" or dAb or a Nanobody® ISV (such as a VHH, including a humanized VHH or camelized VH) or a suitable fragment thereof. [Note: Nanobody® is a registered trademark of Ablynx N.V.]; other single variable domains, or any suitable fragment of any one thereof.

"VHH domains", also known as VHHs, VHH antibody fragments, and VHH antibodies, have originally been described as the antigen binding immunoglobulin variable domain of "heavy chain antibodies" (i.e., of "antibodies devoid of light chains"; Hamers-Casterman et al. 1993 (Nature 363:446-448). The term "VHH domain" has been chosen in order to distinguish these variable domains from the heavy chain variable domains that are present in conventional 4-chain antibodies (which are referred to herein as "VH domains") and from the light chain variable domains that are present in conventional 4-chain antibodies (which are referred to herein as "VL domains"). For a further description of VHH's, reference is made to the review article by Muyldermans 2001 (Reviews in Molecular Biotechnology 74:277-302). For the term "dAb's" and "domain antibody", reference is for example made to Ward et al. 1989 (Nature 341:544), to Holt et al. 2003 (Trends Biotechnol. 21:484); as well as to WO 2004/068820, WO 2006/030220, WO 2006/003388. It should also be noted that, although less preferred in the context of the present invention because they are not of mammalian origin, single variable domains can be derived from certain species of shark (for example, the so-called "IgNAR domains", see for example WO 2005/18629).

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014 (E). As described in ISO 11608-1: 2014 (E), needle-based injection systems may be broadly distinguished into multi-dose container systems and single-dose (with partial or full evacuation) container systems. The container may be a replaceable container or an integrated non-replaceable container.

As further described in ISO 11608-1: 2014 (E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1: 2014 (E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1: 2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The terms "axial", "radial", or "circumferential" as used herein may be used with respect to a first longitudinal axis of the electronic add-on module, the first portion, the second portion, the drug delivery device, the cartridge, the housing, the cartridge holder or the assembly of the drug delivery device and the electronic add-on module, e.g., the axis which extends through the proximal and distal ends of the cartridge.

"Distal" is used herein to specify directions, ends or surfaces which are arranged or are to be arranged to face or point towards dispensing end of the electronic add-on module or the drug delivery device or components thereof and/or point away from, are to be arranged to face away from or face away from the proximal end. On the other hand, "proximal" is used to specify directions, ends or surfaces which are arranged or are to be arranged to face away from or point away from the dispensing end and/or from the distal end of the electronic add-on module or the drug delivery device or components thereof. The distal end may be the end closest to the dispensing and/or furthest away from the proximal end and the proximal end may be the end furthest away from the dispensing end. A proximal surface may face away from the distal end and/or towards the proximal end. A distal surface may face towards the distal end and/or away from the proximal end. The dispensing end may be the needle end where a needle unit is or is to be mounted to the device, for example. Similarly, a distal element compared to a proximal element is located closer to the dispensing end than to the proximal end. Furthermore, when the electronic add-on module is considered alone, the term "distal" may be used with regard to the more distal end of the electronic add-on module, which is located closer to the dispensing end of the drug delivery device when attached to the drug delivery device, and the term "proximal" may be used with regard to the proximal end of the electronic add-on module, which is located further away from the dispensing end of the drug delivery device when attached to the drug delivery device.

BRIEF DESCRIPTION OF THE FIGURES

In the following, non-limiting, examples of the electronic add-on module, the drug delivery device and the assembly of the drug delivery device and the electronic add-on module are described in more detail by making reference to the drawings, in which.

In the Figures, identical elements and components as well as identical elements and components in different examples or embodiments, i.e. elements and components acting identical or provided for the same purposes but belong to different examples, are provided with the same reference signs.

DETAILED DESCRIPTION

Figure 2:
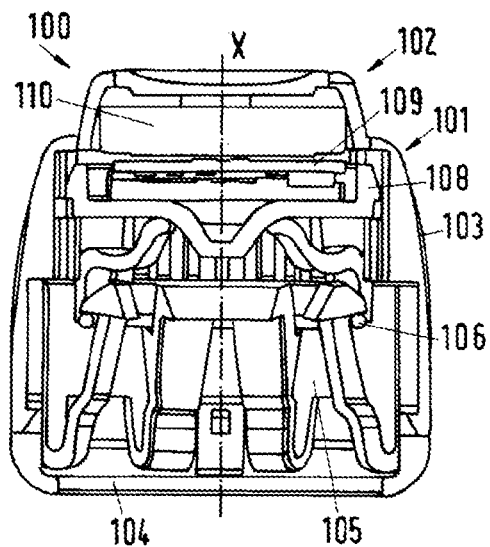
FIG. 2 is a sectional view of the module of FIG. 1.
Figure 1:
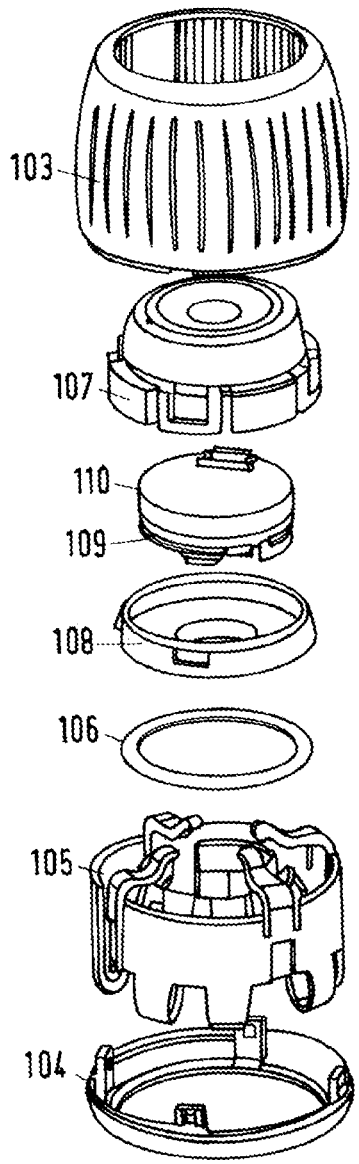
FIG. 1 is an exploded view of the components of a module according to a first embodiment of the present disclosure.
Figure 3:
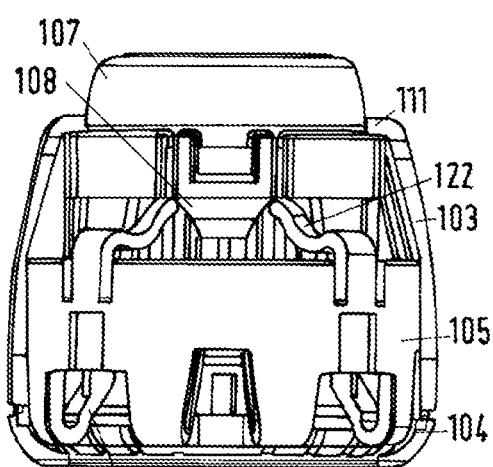
FIG. 3 is a partially cut open view of the module of FIG. 1.

FIGS. 1 to 3 show an exemplary embodiment of an electronic add-on module 100 suitable for releasable attachment to a user interface of a drug delivery device (not shown). The module 100 substantially comprises a first portion 101 and a second portion 102 which are coaxially arranged on a first longitudinal axis X.

The first portion 101 comprises a main housing 103, an end ring 104, a gripper ring 105 and an elastomeric band 106. The second portion 102 comprises an upper button housing 107 and a lower button housing 108, a printed circuit board assembly (PCBA) 109 and a battery 110.

Figure 4:
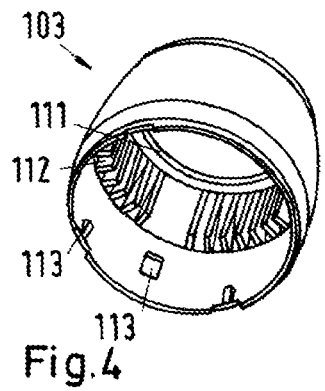
FIG. 4 is a perspective view of the main housing of the module of FIG. 1.

The main housing 103 (see FIG. 4) is a sleeve-like component with an inwardly protruding, ring-shaped flange 111 at its proximal end which limits axial movement of the second portion 102 in the proximal direction. The outer surface of the main housing 103 may be structured, e.g., by ribs and/or grooves as depicted in FIG. 1, to facilitate gripping and rotating the main housing 103. When attached to a drug delivery device, the main housing 103 forms an auxiliary dose dial user interface replicating a dose dial user interface, e.g., a dose dial grip, of the drug delivery device. The main housing 103 has several vertical ribs 112 which axially locate and stabilize the vertical motion of the second portion 102. Further, the main housing 103 has several molded protrusions 113 acting as clip features for assembling other components into the housing.

The end ring 104 features several clip features around the circumference which interact with corresponding protrusions 113 in the main housing 103 and ensure secure attachment. The end ring 104 further provides protection for the lower parts of the gripper ring 105. It comprises an annular shape that has the outer diameter equal to that of the main housing 103 and that gradually decreases towards an opening at the bottom, i.e., at the distal end of the module 100.

Figure 5:
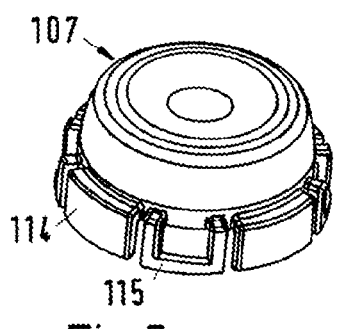
FIG. 5 is a perspective view of an upper button of the module of FIG. 1.

The upper button 107 (see FIG. 5) is one of the two interaction points of the module 100 and is meant to transfer the force applied by the user through the module 100 to the underlying injector pen and initiate injection. It can be molded from a translucent material which would allow light to shine through from the inside if required for providing user feedback. It has a concave section on its proximal top face, which is meant to guide the user's finger to ensure even distribution of the button actuation force. The lower part of the upper button 107 features a locating shoulder 114 configured to abut flange 111 of the main housing and several clips 115 evenly distributed around the circumference. The locating shoulder 114 further ensures accurate positioning of the button assembly within the main housing 103 by interacting with the ribs 112 on the inside surface of the main housing 103.

Figure 6:
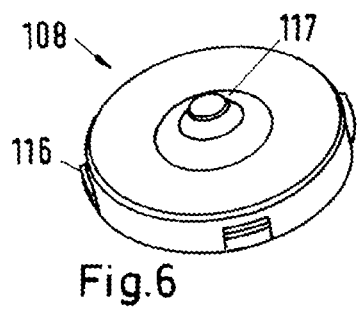
FIG. 6 is a perspective view of a lower button of the module of FIG. 1.

The lower button 108 (see FIG. 6) is manufactured from an injection molded polymer and serves the purpose of containing the electronics assembly of the module. It features several clip features 116 distributed around the circumference of its outer face, which interact with the corresponding clips 115 on the upper button 107 and allow the two parts to be securely fastened together. The lower button 108 also has a protruding truncated conical section 117 at its distal bottom face which acts as the point of contact between the button and the activation button of the injector device the module 100 is attached to.

The upper button 107 and the lower button 108 together form a button assembly housing the electronics 109, 110 for dose detecting. The button assembly can spin freely relative to the main housing 103 and can be axially displaced relative to the main housing 103. However, the axial movement is limited by flange 111 in the proximal direction and by a spring element of the gripper ring 105 in the distal direction.

The gripper ring 105 (see FIGS. 7*a* and 7*b*) is designed for injection molding and can be manufactured using a simple 2-part mold. The gripper ring 105 acts as the interface and adapter between the module 100 and the various injector pens, allowing secure attachment of the module regardless of the injector pen type and size within design limits explained below.

Figure 7A:
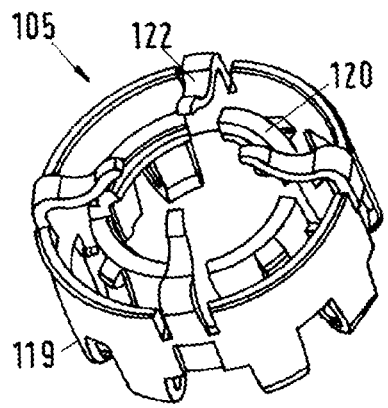
FIGS. 7*a,b* are perspective views of a gripper ring of the module of FIG. 1.
Figure 7B:
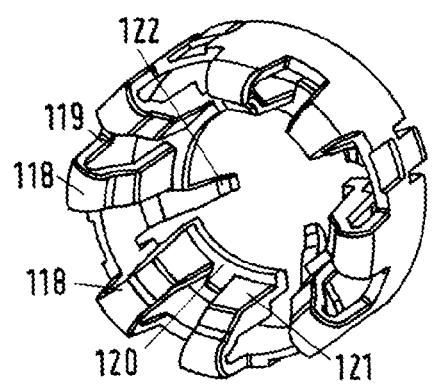

In the depicted example, the gripper ring 105 comprises eight elastically deformable, i.e., flexible, cantilever arms 118 attached to an annular outer sleeve-like portion of gripper ring 105 and positioned so that in their nominal position as depicted in FIGS. 7*a* and 7*b*, the inner diameter of the interior faces of the gripper ring is between about 14 mm to about 15 mm. This is smaller than the smallest injector dial grip of the above cited prior art drug delivery devices.

Each of the flexible arms 118 extends distally from a first end 119 at the distal edge of the sleeve-like portion of gripper ring 105, is bent by about 160° inwardly and extends in the proximal direction up to a free end 120 which is formed as an inwardly protruding shoulder. The arms 118 are arranged in pairs and every pair of flexible arms 118 is connected in pairs at their free ends 120, which provides better stiffness of the interface. The shoulder feature at the free ends 120 provides a hard limit to the axial movement of the drug delivery device (see FIGS. 8*a* and 8*b*) and ensures repeatable positioning of the module 100. The inner surface of the gripper arms 118 also features a stepped profile with a clamping section 121, which enables easier location and reduces insertion force at the beginning stage of attachment, while gradually increasing it as the movement continues. The clamping sections 121 may be provided with rubber elements to increase friction with a component of the drug delivery device.

Figure 8A:
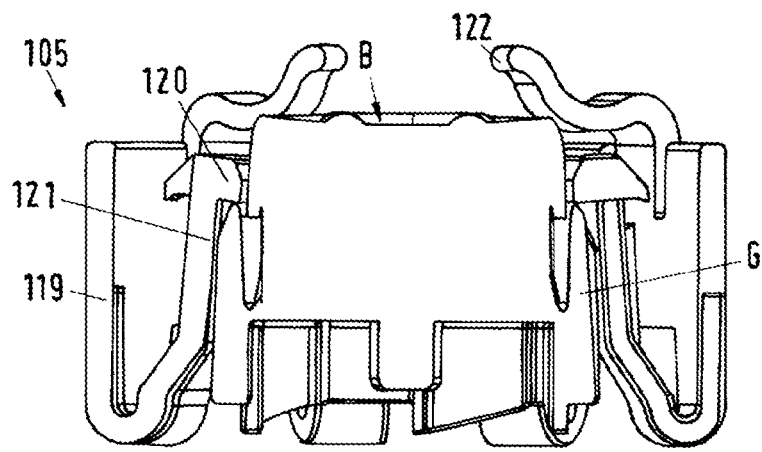
FIGS. 8*a, b* are sectional views of the gripper ring when attached to different drug delivery devices.
Figure 8B:
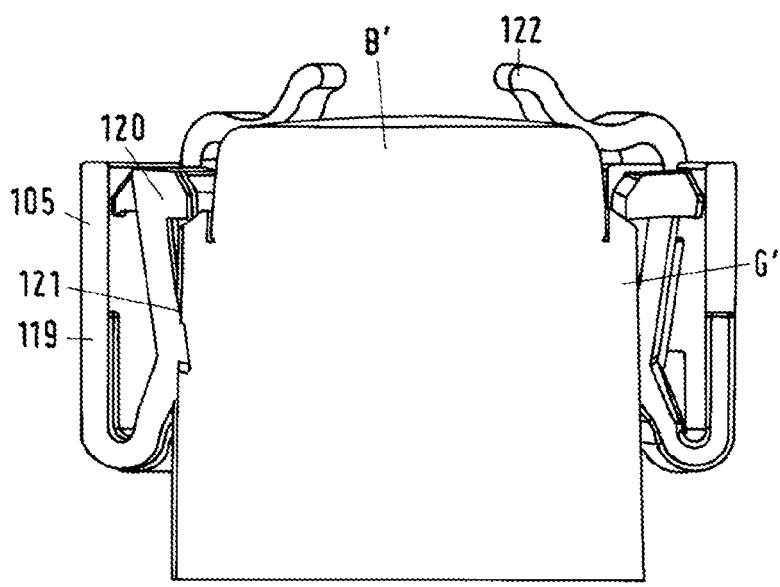

FIGS. 8*a* and 8*b* show the module 100 attached to a schematically indicated proximal end of two different drug delivery devices. The drug delivery device of FIG. 8*a* comprises a dose dial user interface, e.g., a dial grip G, and an injection user interface, e.g., a dose button B. The drug delivery device of FIG. 8*b* comprises a dose dial user interface, e.g., a dial grip G', and an injection user interface, e.g., a dose button B'. Comparing FIGS. 8*a* and 8*b* shows that the dial grip G has a relatively smaller diameter whereas the diameter of dial grip G' is relatively larger. In addition, dose button B has a smaller diameter than dose button B'.

The module 100 according to the present disclosure has the ability to be attached to many different drug delivery devices with different shapes and sizes as exemplary indicated in FIGS. 8*a* and 8*b* without the need to use adapters. In addition, the overall size of the module 100 may be kept small and easy to handle. This makes the module 100 more accessible to a wider group of patients because it minimizes the number of changes to the patients' existing usage habits.

The gripping mechanism according to the present disclosure allows attachment to dose dial user interfaces, e.g., dial grip G or dial grip G', and injection user interfaces, e.g., dose button B or dose button B', of varying diameters and shapes. To achieve this, the clamping sections 121 of the arms 118 are configured to be elastically deflected radially outwards with respect to the longitudinal axis X of the module 100 from the unstressed, nominal position depicted in FIGS. 7a and 7b to a strained deflected position. While the clamping sections 121 circumvent in their nominal position a cavity configured to receive a portion of the drug delivery device which cavity has a diameter of 14 mm to 15 mm, the degree of deflection of the arms may vary depending on the shape and dimensions of the drug delivery device interface to which the module 100 is attached. For example, FIGS. 8a and 8b show that when the arms 118 are in their deflected position the cavity may have a diameter of about 15 mm (FIG. 8a) to 19 mm (FIG. 8b). The deflection of the clamping sections 121 is limited to a maximum deflected position defined by radial abutment of the arms 118 at the annular outer sleeve-like portion of gripper ring 105. When in their maximum deflected position, the cavity defined by the clamping sections 121 may have a diameter of e.g., about 19 mm to 21 mm.

At the top of the gripper ring 105 there are four integral plastic leaf springs 122, which hold the second portion 102, i.e., the shuttling button assembly, in place while at rest and return it to its neutral position after actuation.

The elastomeric band 106 wraps around the circumference of the gripper arms 118 and is retained by clip features of the arms 118. The band 106 provides a compressive force that bends the arms 118 radially inwards towards the longitudinal axis X. When the module 100 is attached to an injector pen dial grip, this increases the friction force and ensures a more secure fit. Further, the band 106 helps return the arms 118 to their nominal position after detachment of the module 100 from a drug delivery device.

The module 100 can be used to add smart capabilities to several different injector pens. The general procedure for using the module 100 is as follows: first, the user attaches the module 100 onto a suitable injector by pressing it axially onto the dial grip. The grip mechanism inside ensures a robust mechanical connection with dials of varying diameters from around 14 mm to 18 mm.

The gripping force of the arms 118 is sufficient to transfer the torque applied from the main housing 103 to the dial grip of the injector, which allows setting the medication dose in a way that is familiar to the user. When the dose is set, the user may press the button 102, which has sufficient axial movement to actuate the injector's button and initiate the injection.

Some of the above-mentioned injector pens comprise dose buttons which rotate as they move distally during an injection stroke. The module 100 accommodates this because the second portion 102 is not constrained rotationally to the first portion 101 and can spin freely with the dose button during the injection stroke. Throughout this procedure, the electronics 109, 110 of the module 100 can measure the rotation angle to infer the selected dose and detect the injection event, e.g., on the basis of click noises generated during dose dispensing which are detected by a microphone or the like acoustic sensor. The module 100 may save the injection information and may later send it e.g., to the user's smartphone. Thus, the module 100 allows patients to track their injection times and dosages to better manage their conditions and share information with their doctors.

REFERENCE NUMERALS 100 electronic add-on module
101 first portion
102 second portion
103 main housing
104 end ring
105 gripper ring
106 band
107 upper button
108 lower button
109 PCBA
110 battery
111 flange
112 rib
113 protrusion
114 shoulder
115 clip
116 clip
117 conical section
118 arm
119 first end
120 free end (shoulder)
121 clamping section
122 leaf spring
X first Longitudinal axis (of the first portion)
G, G' grip (dose dial user interface)
B, B' button (injection user interface)

The invention claimed is:

1. An electronic add-on module configured for attachment to a drug delivery device, the electronic add-on module comprising a first portion with a main housing defining a longitudinal axis, wherein the first portion comprises on an inner side of the main housing at least two elastically deformable arms each having a first end constrained to the main housing and a clamping section which is configured to be elastically deflected radially outwards with respect to the longitudinal axis from an unstressed, nominal position to a strained, deflected position, wherein when the arms are in their nominal position, the clamping sections circumvent a cavity configured to receive a portion of the drug delivery device, wherein the arms are provided on a common gripper ring which is constrained in the main housing, and wherein the common gripper ring comprises at least one leaf spring extending proximally from the common gripper ring.

2. The electronic add-on module according to claim 1, wherein when the arms are in their nominal position the cavity has a diameter of 14 mm to 15 mm and when the arms are in their deflected position the cavity has a diameter of 15 mm to 19 mm.

3. The electronic add-on module according to claim 1, wherein deflection of the clamping sections is limited to a maximum deflected position, wherein when the arms are in their maximum deflected position the cavity has a diameter of 19 mm to 21 mm.

4. The electronic add-on module according to claim 1, wherein the arms comprise a free end opposite to the first end, wherein the free end comprises a shoulder protruding radially inwards with respect to the clamping sections.

5. The electronic add-on module according to claim 4, comprising at least three pairs of the arms, wherein the arms of each pair of arms is connected at the free end by the shoulder.

6. The electronic add-on module according to claim 1, further comprising an elastomeric band wrapped around an outer circumference of the arms and configured to exert a force on the arms deflecting the clamping sections radially inwards with respect to the longitudinal axis from the unstressed, nominal position.

7. The electronic add-on module according to claim 1, wherein the main housing comprises on an inner side snap protrusions configured for rotationally and/or axially constraining component parts of the first portion in the main housing.

8. The electronic add-on module according to claim 1, wherein the main housing comprises on an inner side ribs configured for axially guiding a component part of the module.

9. The electronic add-on module according to claim 1, further comprising a second portion coupled to the first portion allowing relative axial movement parallel to the first longitudinal axis between the first portion and the second portion.

10. The electronic add-on module according to claim 9, wherein the first portion comprises an auxiliary dose dial user interface configured to be attached to a dose dial user interface of the drug delivery device, such that the first portion follows movement of the dose dial user interface and vice versa when attached to the drug delivery device, and wherein the second portion comprises an auxiliary injection user interface configured to apply pressure onto an injection user interface of the drug delivery device.

11. The electronic add-on module according to claim 9, wherein the second portion comprises at least one of an electrical power source, a printed circuit board assembly, a sensor arrangement configured to detect a relative rotational movement between at least two component parts of the drug delivery device, a communication unit for communicating with another device, or a switch arrangement.

12. The electronic add-on module according to claim 11, wherein the second portion comprises the sensor arrangement configured to detect the relative rotational movement between the at least two component parts of the drug delivery device, and the sensor arrangement is an acoustic sensor arrangement.

13. The electronic add-on module according to claim 1, wherein the common gripper ring further comprises at least one leaf spring extending proximally from the common gripper ring, and the leaf spring biases a second portion proximally with respect to the first portion.

14. The electronic add-on module according to claim 13, wherein the second portion is coupled to the first portion in a manner allowing relative axial movement parallel to the first longitudinal axis between the first portion and the second portion.

15. The electronic add-on module according to claim 14, wherein the first portion comprises an auxiliary dose dial user interface configured to be attached to a dose dial user interface of the drug delivery device, such that the first portion follows movement of the dose dial user interface and vice versa when attached to the drug delivery device, and wherein the second portion comprises an auxiliary injection user interface configured to apply pressure onto an injection user interface of the drug delivery device.

16. The electronic add-on module according to claim 14, wherein second portion comprises an electrical power source, a printed circuit board assembly, a sensor arrangement configured to detect a relative rotational movement between at least two component parts of the drug delivery device, a communication unit for communicating with another device, and/or a switch arrangement.

17. An assembly comprising:
  a drug delivery device comprising:
    a device housing with a container configured to receive a drug or a cartridge filled with a drug,
    a dose setting unit comprising a dose dial user interface at least rotationally moveable with respect to the device housing during dose setting and an injection user interface at least axially moveable with respect to the device housing for causing dose dispensing, and
  a dose delivery unit comprising a plunger at least axially moveable with respect to the device housing during dose dispensing; and an electronic add-on module comprising a first portion with a main housing defining a longitudinal axis, wherein the first portion comprises on an inner side of the main housing at least two elastically deformable arms each having a first end constrained to the main housing and a clamping section which is configured to be elastically deflected radially outwards with respect to the longitudinal axis from an unstressed, nominal position to a strained, deflected position, wherein when the arms are in their nominal position, the clamping sections circumvent a cavity configured to receive a portion of the drug delivery device, wherein the arms are provided on a common gripper ring which is constrained in the main housing, and wherein the common gripper ring comprises at least one leaf spring extending proximally from the common gripper ring, and
  wherein when the electronic add-on module is attached to the dose dial user interface of the drug delivery device, the clamping sections of the arms are elastically biased to abut the dose dial user interface in a form fit and/or friction fit.

18. The assembly according to claim 17, wherein the drug delivery device comprises a clicker mechanism generating an acoustic feedback signal at least during dose setting.

19. An electronic add-on module configured for attachment to a drug delivery device, the electronic add-on module comprising a first portion with a main housing defining a longitudinal axis, wherein the first portion comprises on an inner side of the main housing at least two elastically deformable arms each having a first end constrained to the main housing and a clamping section which is configured to be elastically deflected radially outwards with respect to the longitudinal axis from an unstressed, nominal position to a strained, deflected position, wherein when the arms are in their nominal position, the clamping sections circumvent a cavity configured to receive a portion of the drug delivery device, wherein the arms are provided on a common gripper ring that comprises at least one leaf spring extending proximally from the common gripper ring, and wherein the leaf spring biases a second portion proximally with respect to the first portion.

* * * * *